United States Patent [19]

Cumbo

[11] 4,024,197

[45] * May 17, 1977

[54] PRODUCTION OF BUTANEDIOL

[75] Inventors: Charles C. Cumbo, Wilmington; Kamlesh K. Bhatia, Newark, both of Delaware

[73] Assignee: E. I. Du Pont de Nemours and Company, Wilmington, Del.

[ * ] Notice: The portion of the term of this patent subsequent to Dec. 30, 1992, has been disclaimed.

[22] Filed: Dec. 31, 1975

[21] Appl. No.: 645,693

Related U.S. Application Data

[62] Division of Ser. No. 493,741, July 31, 1974, Pat. No. 3,963,754.

[52] U.S. Cl. .......................................... 260/635 E
[51] Int. Cl.² ...................................... C07C 29/00
[58] Field of Search ............................. 260/635 E

[56] References Cited

UNITED STATES PATENTS

| | | | |
|---|---|---|---|
| 2,122,813 | 7/1938 | Groll et al. | 26/635 E |
| 2,566,559 | 9/1951 | Dolnick et al. | 260/615 A |
| 2,808,440 | 10/1957 | Dickey et al. | 260/635 E |
| 2,888,492 | 5/1959 | Fischer et al. | 260/635 E |
| 3,102,899 | 9/1963 | Cannell | 260/632 HF |
| 3,239,566 | 3/1966 | Slaugh et al. | 260/632 HF |
| 3,394,170 | 7/1968 | Kohll | 260/635 A |
| 3,929,915 | 12/1975 | Cumbo et al. | 260/635 E |
| 3,933,920 | 1/1976 | Neinburg et al. | 260/635 A |

*Primary Examiner*—Joseph E. Evans

[57] ABSTRACT

2-vinyl-5-methyl-1,3-dioxane is provided as a new cyclic acetal which, when hydroformylated, hydrolyzed and hydrogenated provides high yields of a mixture of 1,4-butanediol and 2-methyl-1,3-propanediol.

9 Claims, No Drawings

PRODUCTION OF BUTANEDIOL

This is a divisional application of copending application Ser. No. 493,741, filed July 31, 1974, now U.S. Pat. No. 3,963,759.

BACKGROUND OF THE INVENTION

This invention relates to a unique cyclic acetal which is particularly useful for preparing an advantageous diol product upon the hydrolysis and hydrogenation of the hydroformylation reaction product of the acetal.

There are many cyclic acetals which may be hydroformylated and then hydrolyzed and hydrogenated to yield polyols, including diols. These prior art cyclic acetals yield a polyol product containing three or more polyols after completion of the reaction sequence described above. Because the polyols in any such admixture have very similar physical properties, the separation of the mixture into its component parts is extremely difficult in many cases.

SUMMARY OF THE INVENTION

It has now been found that 2-vinyl-5-methyl-1,3-dioxane (VMD) is a new cyclic acetal which possesses novel properties and yields advantages which cannot be obtained from prior art cyclic acetals. In particular, the acetal of this invention, when hydroformylated, hydrolyzed and hydrogenated, provides high yields of a unique mixture of only two polyols, 1,4-butanediol (BAD) and 2-methyl-1,3-propanediol (MPD), which can be easily and simply separated from one another. The acetal of this invention exists in the cis and trans forms.

DETAILED DESCRIPTION OF THE INVENTION

The new cyclic acetal (VMD) of this invention has the structure

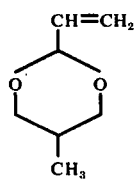

Acetal Formation

VMD can be prepared, for example, by reacting acrolein with MPD using conventional reaction conditions. Such conditions are discussed in U.S. Pat. Nos. 2,729,650 issued Jan. 3, 1956 to Habeshaw et al.; 2,840,615 issued June 24, 1958 to Stautzenberger, 2,987,524 issued June 6, 1961 to Fischer et al.; 2,566,559 issued Sept. 4, 1951 to Dolnick and Potash and the like. As described in U.s. Pat. No. 2,566,559, acrolein is reacted with MPD at a molar ratio of MPD:acrolein of 4 or 5:1.

In one preferred process, the acrolein is reacted with MPD in a suitable solvent such as benzene and in the presence of a weak acid catalyst such as a small amount of polyphosphoric acid with the azeotropic distillation of water.

The acrolein may be obtained commercially or it may be prepared from propylene, for example, as described in U.S. Pat. Nos. 3,065,264 and 3,087,964 issued Nov. 20, 1962 and Apr. 30, 1963, respectively, to Koch et al.; 3,387,038 issued June 4, 1968 to Koch; 3,799,978 issued Mar. 26, 1974 to O'Hara et al. and so on. In such processes, propylene is oxidized in the presence of water and oxygen to yield acrolein using molybdenum containing catalysts, generally bismuth molybdates.

The MPD with which the acrolein is reacted is obtained directly from the hydrolysis/hydrogenation of the aldehyde of VMD. It can also be obtained by reacting acrolein with other diols and then hydroformylating and hydrolyzing and hydrogenating the reaction product, but only in very small yields.

Hydroformylation

The new cyclic acetal of this invention is particularly advantageous when used in a reaction sequence involving hydroformylation, hydrogenation and hydrolysis. In the first of these reactions, the VMD is reacted with hydrogen and carbon monoxide using conventional hydroformylation reaction conditions to yield the corresponding aldehyde. Conventional reaction conditions are disclosed in U.S. Pat. Nos. 3,527,809 issued Sept. 8, 1970 to Pruett et al.; 2,880,241 issued Mar. 31, 1959 to V. L. Hughes; 2,729,650 issued Jan. 3, 1956 to Habeshaw et al.; 3,239,566 issued Mar. 8, 1966 to L. H. Slaugh and R. D. Mullineaux; British Pat. No. 801,734 issued Sept. 17, 1958 to Esso Research and Engineering and the like.

In a preferred process, VMD is reacted in either a continuous or batch reaction with hydrogen and carbon monoxide at a molar ratio of $H_2:CO$ of 0.9:1 to 1.2:1, preferably 1:1. At ratios lower than 0.9:1, the reaction rates are too slow for commercial utility; at ratios higher than 1.2:1, hydrogenation of VMD occurs as an undesired side reaction. Best yields are obtained at the preferred ratio.

The preferred hydroformylation reaction is carried out in the presence of a rhodium carbonyl complex catalyst at a molar ratio to VMD of $0.5 \times 10^{-3}:1 - 6.0 \times 10^{-3}:1$, preferably $1 \times 10^{-3}:1 - 2 \times 10^{-3}:1$. At the preferred ratios, optimum yields and reaction rates result. The rhodium complex catalyst forms in situ when rhodium in the form of $Rh_6(CO)_{16}$ is added to the hydroformylation reaction mixture containing the ligand described below. The same rhodium carbonyl complex with a trialkyl phosphite may also be prepared first and then added to the reaction mixture.

The phosphite ligand used in the hydroformylation reaction has the formula

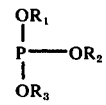

wherein $R_1$, $R_2$ and $R_3$ are the same or different alkyl groups having 1 – 12 carbon atoms such as, for example, methyl, ethyl, propyl, octyl, pentyl, decyl, dodecyl and the like or phenyl. For ease of operation, it is preferred that $R_1$, $R_2$ and $R_3$ are the same. Most preferably, $R_1$, $R_2$ and $R_3$ are the same alkyl groups having 1 – 3 carbon atoms such as trimethyl phosphite, triethyl phosphite, tri-n-propyl phosphite and triisopropyl phosphite since these materials are low boiling and easily separated, purified and recycled into the system. However, higher boiling phosphites within the scope of the above formula may also be used including tri-n-butyl phosphite, triisooctyl phosphite, dimethyldodecyl phosphite, tridecyl phosphite, triphenyl phosphite, methylethylpropyl phosphite, dimethyl phenyl phosphite, methylpropyl phenyl phosphite as well as any other combination within the definition of the above formula and mixtures of any of them.

The phosphite ligand forms a complex with rhodium and carbon monoxide as described in U.S. Pat. No. 3,527,809, and this complex catalyzes the hydroformylation reaction. An excess of the phosphite over that which is required to complex with the rhodium must be used in order to prevent isomerization of the double bond in the VMD and to maximize the yield of linear aldehyde produced in the reaction. The excess ligand is also necessary to insure the stability of the rhodium catalyst throughout the reaction. Generally, a molar ratio of phosphite ligand to rhodium of from 5:1 — 50:1 is employed. In order to obtain optimum reaction rates and produce a product which will favor the formation of butanediol upon hydrolysis and hydrogenation, it is preferred that a ligand:rhodium molar ratio of from 10:1 — 20:1 be employed.

The hydroformylation reaction may be carried out batchwise or continuously as desired in any suitable reactor including a simple low pressure reactor. For ease of operation, it is preferred that the reaction be carried out in a continuous stage reactor through which the acetal flows concurrently to the flow direction of the carbon monoxide and hydrogen gas. The reactor pressure should be from about 75 – 150 psig, preferably 100 – 110 psig. The reactor temperature should be from about 85° – 115° C., preferably 100° – 110° C. and the residence time in the reactor should be from 0.5 – 5 hours, preferably 1 – 2 hours. At the preferred conditions, the highest yields and best reaction rates are obtained.

After product stream exits from the reactor, the ligand is stripped off in any suitable manner. When the preferred ligands of this invention are used, the reaction product is preferably fed into a ligand stripper column maintained at a pressure of 10 mm. and a temperature of 110° C. Excess ligand is removed and recycled to the reactor. The product stream is then fed to an aldehyde vaporizer column maintained at a pressure of about 8 mm. and a temperature of 120° C. Aldehyde product is distilled off to be used in the hydrolysis - hydrogenation reaction. In order to prevent aldehyde decomposition, the temperature in this step should not exceed 120° C. and the aldehyde residence time should be less than five minutes. The bottom stream from this separation step contains some high boiling by-products which are unavoidably formed as well as all of the rhodium catalyst. This stream is recycled to the reactor after removing a small portion, about one-eighth, of the stream as a purge stream to control the buildup of high boilers. While it has been disclosed that the presence of these high boiling constituents is advantageous in some cases such as, for example, disclosed in U.S. Pat. No. 3,527,809 issued to Pruett on Sept. 8, 1970, it has been found that an acceptable maximum concentration of high boilers in this invention is about 50%, preferably 25%.

Hydrolysis/Hydrogenation

The hydroformylation product can be hydrolyzed and hydrogenated using any conventional procedure such as those described in U.S. Pat. Nos. 2,729,650 issued Jan. 3, 1956 to Habeshaw et al.; 2,888,492 issued May 26, 1959 to Fischer et al.; 2,721,223 issued Oct. 18, 1955 to Arundale and Mikeska and the like. In a preferred process, water is mixed with the acetal-aldehyde hydroformylation reaction product and the mixture is fed into a hydrogenation reactor at a temperature of 30° – 130° C., a pressure of 100 – 5,000 psig and at a water:aldehyde molar ratio of 1:1 – 20:1. The aldehyde functional group is reduced to the corresponding alcohol in the presence of a catalytic amount of any hydrogenation catalyst such as Raney nickel, for example. As the reaction is continued, the acetal ring is thought to split to yield BAD and MPD which can be separated from one another by conventional distillation techniques. The MPD can then be recycled and used in the preparation of the cyclic acetal of this invention. The BAD can be refined for use as such, for example, as a cross-linking agent in preparing polyurethane polymers, or it can be heated in a cyclization column, for example, to produce tetrahydrofuran.

The invention is further illustrated but is not intended to be limited by the following examples in which all parts and percentages are by weight unless otherwise specified.

Preparation of 2-vinyl-5-methyl-1,3-dioxane (VMD)

About 45 g. (0.5 mole) of MPD are reacted with 30.8 g. (0.55 mole) of acrolein in 100 ml of benzene in the presence of 0.2 g. of polyphosphoric acid as a catalyst with the azeotropic distillation of water, for thirty minutes or until water distillation ceases. The liquid product is removed and analyzed by gas-liquid phase chromatography. The analysis of the product show 87% conversion to VMD. The distilled VMD product has a boiling point of 62° C. at 24 mm.

EXAMPLE 1

Hydroformylation

Into a 400 cc. lined glass autoclave equipped with a stirrer are charged, in an atmosphere of dry nitrogen, 15.4 g. (0.12 mole) of VMD [69% trans and 31% cisisomer], 0.025 g. (2.3 × 10$^{-5}$ mole) of hexarhodium hexadecacarbonyl and 250 μl. of trimethyl phosphite. The molar ratio of trimethyl phosphite to rhodium is 14.3:1. The autoclave is then charged with a 1:1 molar ratio of carbon monoxide-hydrogen gas to a pressure of 95 psig. The contents are heated to 110° C. and the pressure is adjusted to 105 psig, and maintained throughout the reaction. After 55 minutes 96% of the theoretical amount of gas is absorbed by the reaction mixture. At the end of that time the autoclave is cooled and the excess gases are vented. The liquid contents are removed and analyzed by gas-liquid phase chromatography. Analysis of the product shows a 97% conversion of VMD to the following products at the mole percentages specified.

| 2(3'-propanal)-5-methyl-1,3-dioxane | 2(2'-propanal)-5-methyl-1,3-dioxane |
|---|---|
| 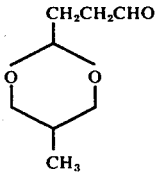 | 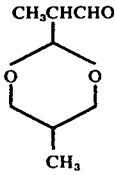 |
| 80% | 12% |
| A | A |

-continued

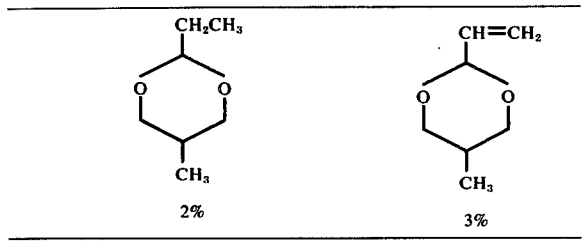

| 2% | 3% |

The aldehydes have a normal/iso ratio of 87/13.

Hydrolysis/Hydrogenation 36.4 g. of the aldehydes prepared above are mixed with 30 ml of a 10% aqueous acetic acid solution and hydrolyzed and hydrogenated at 100° C. and 1000 psig of hydrogen using 3 g. of palladium on charcoal. The reaction product is filtered and the water and acetic acid removed by distillation. Gas-liquid phase chromatographic analysis shows that only MPD (96% yield) and BAD (98% yield) are formed in the reaction.

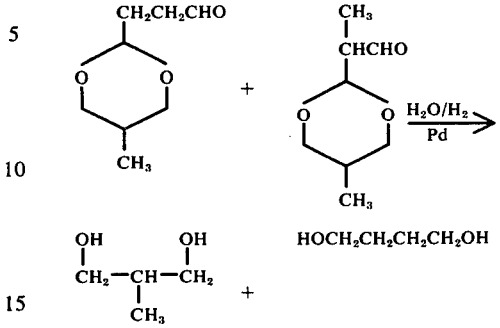

EXAMPLES 2–6

Example 1 is repeated except that cyclic acetals other than VMD are used in the hydroformylation reaction of Examples 3–6.

TABLE I

| Ex. | Compound | Ligand | Ligand/Rh | Reaction Time | Products (mole %) | | | |
|---|---|---|---|---|---|---|---|---|
| | | | | Hydroformylation | | | | |
| 2 | 2-vinyl-5-methyl-1,3-dioxane 15.4 g, 0.12 mole | 200 μl (CH₃O)₃P | 11.4:1 | 53 min. | [structure A] 76% A | [structure B] 10% B | [structure] 4% | [structure] 4% |
| 3 | 2-vinyl-5,5-dimethyl-1,3-dioxane 17.1 g, 0.12 mole | 250 μl (CH₃O)₃P | 14.3:1 | 56 min. | [structure A] 76% A | [structure B] 12% B | [structure] 3% | [structure] 5% |
| 4 | 2-vinyl-4,4,6-trimethyl-1,3-dioxane 18.8 g, 0.12 mole | 250 μl (CH₃O)₃P | 14.3:1 | 60 min. | [structure A] 77% A | [structure B] 12% B | [structure] 2% | [structure] 5% |
| 5 | 2-vinyl-4-methyl-1,3-dioxane 15.4 g, 0.12 mole | 250 μl (CH₃O)₃P | 14.3:1 | 43 min. | [structure A] 76% A | [structure B] 14% B | [structure] 8% | [structure] 3% |

TABLE I-continued

| | | | Ligand/ | Re-action | Hydroformylation | | | |
|---|---|---|---|---|---|---|---|---|
| Ex. | Compound | Ligand | Rh | Time | Products (mole %) | | | |
| 6 | 2-vinyl-4-methyl-1,3-dioxolane 13.7 g, 0.12 mole | 250 μl (CH₃O)₃P | 14.3:1 | 52 min. | CH₂CH₂CHO 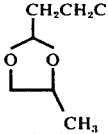 81 % A | CH₃ CHCHO 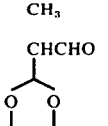 7 % B | CH=CH₂ 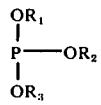 1 % | CH₂CH₃ 3 % |

TABLE II

| Example | Amount A and B | Hydrolysis/Hydrogenation % Conversion A | % Conversion B | Products (mole %) | |
|---|---|---|---|---|---|
| 2 | 36.4 g. (0.23 mole) (87% A, 13% B) | 86 | 42 | C<br>D | 1,4-butanediol (70.2)<br>2-methyl-1,3-propanediol (71.6) |
| 3 | 39.6 g. (0.23 mole) (86% A, 14% B) | 90 | 50 | C<br>D<br>E | 1,4-butanediol (73.5)<br>2-methyl-1,3-propanediol (6.5)<br>2,2-dimethyl-1,3-propanediol (80.0) |
| 4 | 42.8 g. (0.23 mole) 87% A, 13% B | 90 | 50 | C<br>D<br>E | 1,4-butanediol (74.4)<br>2-methyl-1,3-propanediol (6.2)<br>2-methyl-2,4-pentanediol (80.6) |
| 5 | 36.4 g (0.23 mole) 87% A, 13% B | 87 | 45 | C<br>D<br>E | 1,4-butanediol (71.9)<br>2-methyl-1,3-propanediol (5.8)<br>1,3-butanediol (77.6) |
| 6 | 33.2 g. (0.23 mole) 87% A, 13% B | 90 | 50 | C<br>D<br>E | 1,4-butanediol (74.4)<br>2-methyl-1,3-propanediol (6.0)<br>1,2-propanediol (79.0) |

By contrast to the results in Examples 1 and 2, the acetals of Examples 3–6, after being hydroformylated, hydrolyzed and hydrogenated, yield more than two diols. Further, in each of Examples 3–6, the diols produced other than BAD are not suitable for use in the preparation of the VMD of this invention as is the MPD of Examples 1 and 2.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. A process for the preparation of 1,4-butanediol and 2-methyl-1,3-propane diol by hydroformylating 2-vinyl-5-methyl-1,3-dioxane with carbon monoxide and hydrogen in the presence of a hydroformylation catalyst under conventional conditions and then hydrogenating and hydrolyzing the hydroformylation reaction product, in the presence of water and a hydrogenation catalyst under conventional conditions.

2. The process of claim 1 wherein the 2-vinyl-5-methyl-1,3-dioxane is hydroformylated by reacting it with hydrogen and carbon monoxide for about one-five hours at a molar ratio of $H_2$:CO of 0.9:1 – 1.2:1 in the presence of a rhodium carbonyl catalyst at a molar ratio to the cyclic acetal of $0.5 \times 10^{-3} - 6.0 \times 10^{-3}$ and a phosphite having the formula $$\begin{array}{c} OR_1 \\ | \\ P-OR_2 \\ | \\ OR_3 \end{array}$$

wherein $R_1$, $R_2$ and $R_3$ are the same or different alkyl groups having 1 – 12 carbon atoms or phenyl at a molar ratio to the rhodium catalyst of about 5:1 – 50:1 at a temperature of 85° – 110° C and a pressure of about 75 – 150 psig.

3. The process of claim 2 wherein $R_1$, $R_2$ and $R_3$ are the same alkyl groups having 1–3 carbon atoms.

4. The process of claim 2 wherein the reaction is carried out for about 1 – 2 hours.

5. The process of claim 2 wherein the molar ratio of $H_2$:CO is 1:1.

6. The process of claim 2 wherein the molar ratio of the rhodium catalyst to the cyclic acetal is $1 \times 10^{-3} - 2 \times 10^{-3}$.

7. The process of claim 2 wherein the molar ratio of the phosphite to the rhodium catalyst is 10:1 – 20:1.

8. The process of claim 2 wherein the temperature is 100° – 110° C. and the pressure is 100 – 110 psig.

9. The process of claim 1 wherein the hydroformylation reaction product is mixed with water at a molar ratio of water to reaction product of 1:1 – 20:1 and then hydrolyzed and hydrogenated in the presence of a catalytic amount of a hydrogenation catalyst at a temperature of 30° – 130° C. and a pressure of 100 – 5,000 psig.

* * * * *

UNITED STATES PATENT OFFICE
CERTIFICATE OF CORRECTION

PATENT NO. : 4,024,197
DATED : MAY 17, 1977
INVENTOR(S) : CHARLES C. CUMBO and KAMLESH K. BHATIA It is certified that error appears in the above-identified patent and that said Letters Patent are hereby corrected as shown below:

Column 1, line 6, "3,963,759" should be -- 3,963,754 --.

Column 1, line 57, "U.s." should be -- U.S. --.

Column 4, line 67, "A" second occurrence should be -- B --.

*Signed and Sealed this*

*Twenty-seventh* Day of *September 1977*

[SEAL]

Attest:

RUTH C. MASON
*Attesting Officer*

LUTRELLE F. PARKER
*Acting Commissioner of Patents and Trademarks*